United States Patent

Fujiwara et al.

Patent Number: 5,804,590
Date of Patent: Sep. 8, 1998

[54] TREATMENT AND PROPHYLAXIS OF OSTEOPOROSIS

[75] Inventors: Toshihiko Fujiwara, Ebina; Masaaki Miyamoto, Fujisawa; Hiroyoshi Horikoshi, Funabashi, all of Japan

[73] Assignee: Sankyo Company, Limited, Tokyo, Japan

[21] Appl. No.: 770,554

[22] Filed: Dec. 23, 1996

[30] Foreign Application Priority Data

Dec. 26, 1995 [JP] Japan ................................. 7-338440

[51] Int. Cl.[6] ................................................ A61K 31/425
[52] U.S. Cl. ............................................ 514/369; 514/370
[58] Field of Search ...................................... 514/369, 370

[56] References Cited

U.S. PATENT DOCUMENTS

| | | | |
|---|---|---|---|
| 4,572,912 | 2/1986 | Yoshioka et al. | 514/369 |
| 4,687,777 | 8/1987 | Meguro et al. | 514/342 |
| 5,317,029 | 5/1994 | Inazu et al. | 514/422 |
| 5,338,855 | 8/1994 | Yoshioka et al. | 514/369 |
| 5,407,947 | 4/1995 | Bryant et al. | 514/320 |
| 5,436,257 | 7/1995 | Fujita et al. | 514/369 |
| 5,476,865 | 12/1995 | Panetta et al. | 514/369 |
| 5,576,340 | 11/1996 | Fujita et al. | 514/369 |
| 5,578,620 | 11/1996 | Fujita et al. | 514/370 |

FOREIGN PATENT DOCUMENTS

| | | |
|---|---|---|
| 0 136 569 | 4/1985 | European Pat. Off. |
| 0 543 662 | 5/1993 | European Pat. Off. |
| 0 547 545 | 6/1993 | European Pat. Off. |
| 0 549 365 | 6/1993 | European Pat. Off. |
| 0 549 366 | 6/1993 | European Pat. Off. |
| 0 590 793 | 4/1994 | European Pat. Off. |
| 0 652 007 | 5/1995 | European Pat. Off. |
| 0 676 398 | 10/1995 | European Pat. Off. |
| 0 678 511 | 10/1995 | European Pat. Off. |
| 0 691 129 | 1/1996 | European Pat. Off. |
| 0 708 098 | 4/1996 | European Pat. Off. |
| 0 745 600 | 12/1996 | European Pat. Off. |
| 5-213763 | 8/1993 | Japan. |
| 7-2848 | 1/1995 | Japan. |
| 7-258132 | 10/1995 | Japan. |
| 8-92249 | 4/1996 | Japan. |
| 8-157461 | 6/1996 | Japan. |

OTHER PUBLICATIONS

Lee et al., Diabetes, 43(12), 1435–9 (Abstract), 1994.

C. Jennermann et al, "Effects of Thiazolidinediones on Bone Turnover in the Rat", Journal of Bone and Mineral Research, vol. 10, Supplement 1, Aug. 1995.

*Primary Examiner*—Leonard Schenkman
*Attorney, Agent, or Firm*—Frishauf, Holtz, Goodman, Langer & Chick, P.C.

[57] ABSTRACT

Compounds of formula (I):

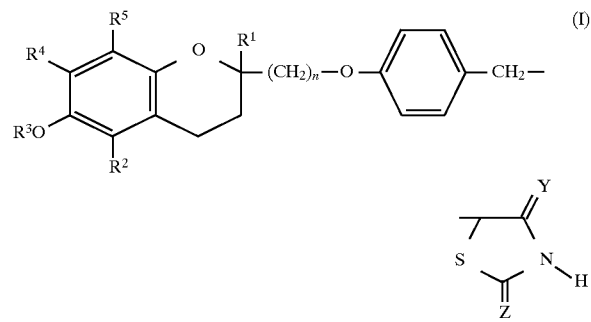

where $R^1$, $R^2$, $R^4$ and $R^5$ are hydrogen or alkyl and $R^3$ is hydrogen, alkyl or various organic groups are effective against osteoporosis at doses at which they also effectively control diabetes.

41 Claims, No Drawings

TREATMENT AND PROPHYLAXIS OF OSTEOPOROSIS

BACKGROUND TO THE INVENTION

The present invention relates to a new use for a series of known thiazolidine derivatives in the treatment and prophylaxis of osteoporosis, especially in patients also suffering from diabetes or pre-diabetic or diabetic-related conditions.

Osteoporosis is frequently observed in older patients, the numbers of whom are increasing, and especially in post-menopausal women. The number of diabetic patients has also been increasing in recent years. Accordingly, the number of patients suffering both osteoporosis and diabetes has shown a considerable increase. As a result, the treatment and prophylaxis of osteoporosis, especially in diabetic patients, has recently become of increasing importance.

Although it is not known whether there is a direct causal relationship between some types of diabetes and osteoporosis, a number of mechanisms has been suggested as the cause of osteoporosis in diabetic patients, for example the following:

- an increase in calcium excretion due to hyperglycemia-induced osmotic diuresis;
- a decrease in renal calcium reabsorption due to a disorder in the vitamin D metabolism;
- a decrease in calcium absorption from the digestive tract;
- a decrease in bone metabolism due to chronically decreased magnesium and due to dysfunction of the parathyroid hormone;
- a decrease in bone formation, or deficiency of insulin action.

However, because the cause of diabetes-related osteoporosis has not yet been established, adequate methods of therapy and prevention have not been determined.

Many thiazolidine derivatives are known for the treatment and prophylaxis of diabetes. Examples of such compounds are disclosed in EP 678 511, EP 676 398, EP 590 793, EP 543 662, EP 549 366, EP 549 365, EP 708 098 and U.S. Pat. No. 4,687,777. Of these, the compounds structurally closest to the compounds of the present invention are believed to be those disclosed in EP 676 398. Several of the prior art documents suggest that the compounds disclosed therein can be used for the treatment and/or prophylaxis of osteoporosis as well as of diabetes. However, a recent report [J. Bone & Mineral Research, 10(1), S361 (1995), Abstract of a paper entitled "Effects of thiazolidinediones on bone turnover in the rat" by C. Jennermann et al.] has suggested that, far from assisting in the treatment and/or prophylaxis of osteoporosis, these thiazolidine derivatives, particularly pioglitazone, one of the leading candidates for commercialisation, actually lead to bone loss, as assessed by a decrease in bone mineral density ("BMD"), thus increasing osteoporosis.

We have now found that these prior art compounds are capable of treating both osteoporosis and diabetes, although not simultaneously, since the anti-diabetic and anti-osteoporosis effects are exhibited at different dosages. Specifically, the dosages of the prior art compounds referred to above at which they are effective against osteoporosis are significantly lower than those required for the treatment of diabetes. Indeed, at the doses at which these prior art compounds are effective against diabetes, they cause a reduction in bone mineral density. At the doses at which they are effective against osteoporosis, they are ineffective, or only partially effective against diabetes. Since, as explained above, diabetes and osteoporosis are often seen simultaneously in the same patient, the physician would have the choice of either treating the diabetes and not treating osteoporosis with these drugs (and often running the risk of aggravating the osteoporosis) or treating the osteoporosis with these drugs, but in a dose not sufficient to treat the diabetes. Effectively, this means that patients with both osteoporosis and diabetes cannot be treated for either disorder with these drugs.

However, we have now surprisingly found that a certain limited class of known thiazolidine derivatives can be used for the treatment and prophylaxis of both osteoporosis and diabetes or pre-diabetic or diabetic-related conditions, and that, with this limited class of thiazolidine derivatives, at the dose at which they are wholly effective against diabetes, they are also effective against osteoporosis.

The compounds employed in the present invention are certain of those disclosed in Japanese Patent Kokai Application Sho 60-51189, U.S. Pat. No. 4,572,912 and European Patent No. 139 421, where they have been suggested for use in the treatment and prophylaxis of diabetes, but not of osteoporosis.

BRIEF SUMMARY OF INVENTION

It is, therefore, an object of the present invention to provide a series of thiazolidine derivatives which are capable of being used as anti-osteoporosis and anti-diabetic drugs at the same time and in the same patient.

Other objects and advantages of the present invention will become apparent as the description proceeds.

The compounds which may be employed in the present invention are those compounds of formula (I):

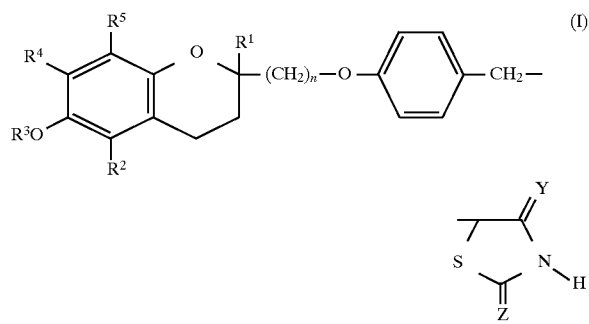

wherein:

$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms;

n is 1, 2 or 3;

Y and Z are the same as or different from each other and each represents an oxygen atom or an imino group; and substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

DETAILED DESCRIPTION OF INVENTION

In the compounds of the present invention, where $R^1$ represents an alkyl group having from 1 to 5 carbon atoms, this may be a straight or branched chain alkyl group having from 1 to 5 carbon atoms, and examples include the methyl, ethyl, propyl, isopropyl, butyl, isobutyl, sec-butyl, t-butyl, pentyl and isopentyl groups, of which the methyl, ethyl, propyl, isopropyl, butyl, isobutyl and pentyl groups are preferred. Of these, those alkyl groups having from 1 to 4 carbon atoms are more preferred, and the methyl group is most preferred.

Where $R^2$ or $R^5$ represents an alkyl group having from 1 to 5 carbon atoms, this may be a straight or branched chain alkyl group having from 1 to 5 carbon atoms, and examples include the methyl, ethyl, propyl, isopropyl, butyl, isobutyl, sec-butyl, pentyl and isopentyl groups, of which the methyl, ethyl, propyl, isopropyl, butyl, isobutyl and pentyl groups are preferred. Of these, those alkyl groups having from 1 to 3 carbon atoms are more preferred, and the methyl group is most preferred.

Where $R^3$ represents an aliphatic acyl group, this may be a straight or branched chain group having from 1 to 6 carbon atoms, preferably an alkanoyl group having from 1 to 6 carbon atoms, for example a formyl, acetyl, propionyl, butyryl, isobutyryl, valeryl, isovaleryl, pivaloyl or hexanoyl group, of which the formyl, acetyl, propionyl, butyryl, isobutyryl, valeryl and hexanoyl groups are preferred. Those aliphatic acyl groups, particularly those alkanoyl groups, having from 1 to 4 carbon atoms are preferred and the acetyl group is most preferred.

Where $R^3$ represents an aromatic acyl group, this is a benzoyl or naphthoyl group in which the aromatic ring may be unsubstituted or it may be substituted by at least one substituent selected from the group consisting of substituents α, defined above and exemplified below. Examples of such substituents α include:

alkyl groups having from 1 to 4 carbon atoms, which may be straight or branched chain groups, such as the methyl, ethyl, propyl, isopropyl, butyl, isobutyl, sec-butyl and t-butyl groups, of which we prefer the methyl and t-butyl groups;

alkoxy groups having from 1 to 4 carbon atoms, which may be straight or branched chain groups, such as the methoxy, ethoxy, propoxy, isopropoxy, butoxy, isobutoxy, sec-butoxy and t-butoxy groups, of which we prefer the methoxy group;

halogen atoms, such as the fluorine, chlorine, bromine and iodine atoms, of which we prefer the fluorine and chlorine atoms;

hydroxy groups;

amino groups;

alkylamino groups having from 1 to 4 carbon atoms, which may be straight or branched chain groups, such as the methylamino, ethylamino, propylamino, isopropylamino, butylamino, isobutylamino, sec-butylamino and t-butylamino groups, of which we prefer the methylamino group;

dialkylamino groups having from 1 to 4 carbon atoms in each alkyl part, which may be straight or branched chain groups, such as the dimethylamino, diethylamino, dipropylamino, diisopropylamino, dibutylamino, diisobutylamino, di-sec-butylamino, di-t-butylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-t-butylamino, N-ethyl-N-propylamino, N-ethyl-N-isopropylamino, N-ethyl-N-butylamino, N-ethyl-N-isobutylamino, N-ethyl-N-sec-butylamino, N-ethyl-N-t-butylamino, N-propyl-N-isopropylamino, N-propyl-N-butylamino, N-propyl-N-isobutylamino, N-propyl-N-sec-butylamino, N-propyl-N-t-butylamino, N-isopropyl-N-butylamino, N-isopropyl-N-isobutylamino, N-isopropyl-N-sec-butylamino, N-isopropyl-N-t-butylamino, N-butyl-N-isobutylamino, N-butyl-N-sec-butylamino, N-butyl-N-t-butylamino, N-isobutyl-N-sec-butylamino, N-isobutyl-N-t-butylamino and N-sec-butyl-N-t-butylamino groups, of which we prefer the dimethylamino group; and nitro groups.

Where $R^3$ represents a substituted benzoyl or naphthoyl group, there is no particular restriction on the number of substituents, except such as may be imposed by the number of substitutable positions (5 in the case of benzoyl or 7 in the case of naphthoyl) and possibly by steric constraints. However, in general, we prefer from 1 to 3 substituents. Where there is more than one substituent, the substituents may be the same as or different from one another.

Examples of such substituted and unsubstituted benzoyl or naphthoyl groups include the benzoyl, 4-nitrobenzoyl, 3-fluorobenzoyl, 2-chlorobenzoyl, 3,4-dichlorobenzoyl, 4-aminobenzoyl, 3-dimethylaminobenzoyl, 2-methoxybenzoyl, 3,5-di-t-butyl-4-hydroxybenzoyl and 1- and 2-naphthoyl groups. Of these, we prefer the unsubstituted benzoyl and 1-naphthoyl groups, and most prefer the benzoyl group.

Where $R^3$ represents a cycloalkanecarbonyl group, this has from 5 to 7 carbon atoms in the cycloalkane ring, and thus a total of from 6 to 8 carbon atoms in the whole group. Examples of such groups include the cyclopentanecarbonyl, cyclohexanecarbonyl and cycloheptanecarbonyl groups, of which the cyclohexanecarbonyl group is preferred.

Where $R^3$ represents a heterocyclic acyl group, this is a group in which a heterocyclic group is attached to a carbonyl group. The heterocyclic part has from 4 to 7 ring atoms, more preferably 5 or 6 ring atoms, of which from 1 to 3, more preferably 1 or 2 and most preferably 1, are heteroatoms selected from the group consisting of nitrogen, oxygen and sulfur atoms. Where there are 3 hetero-atoms in the heterocyclic group, these are preferably all nitrogen atoms or one or two are nitrogen atoms and, correspondingly, two or one are oxygen and/or sulfur atoms. The heterocyclic group is preferably aromatic. Examples of preferred heterocyclic acyl groups include the furoyl (more preferably 2-furoyl), thenoyl (more preferably 3-thenoyl), 3-pyridinecarbonyl (nicotinoyl) and 4-pyridinecarbonyl (isonicotinoyl) groups.

Where $R^3$ represents a phenylacetyl or phenylpropionyl group which is substituted, preferably on the phenyl group, by at least one halogen substituent, the halogen substituent may be a fluorine, chlorine, bromine or iodine atom, and there may be from 1 to 5 such halogen substituents, preferably from 1 to 3 halogen substituents, and more preferably 1 halogen substituent. Examples of such groups include the p-chlorophenylacetyl, p-fluorophenylacetyl, p-bromophenylacetyl, p-iodophenylacetyl, o-chlorophenylacetyl, o-fluorophenylacetyl, o-bromophenylacetyl, o-iodophenylacetyl, m-chlorophenylacetyl, m-fluorophenylacetyl, m-bromophenylacetyl, m-iodophenylacetyl, 2,4-dichlorophenylacetyl, 2,4-difluorophenylacetyl, 2,4-dibromophenylacetyl, 2,4-diiodophenylacetyl, 3-(p-chlorophenyl)propionyl, 3-(p-fluorophenyl)propionyl, 3-(p-bromophenyl)propionyl, 3-(p-iodophenyl) propionyl, 3-(o-chlorophenyl)propionyl, 3-(o-fluorophenyl)propionyl, 3-(o-bromophenyl)propionyl, 3-(o-iodophenyl)propionyl, 3-(m-chlorophenyl)propionyl, 3-(m-fluorophenyl)propionyl, 3-(m-bromophenyl)propionyl, 3-(m-iodophenyl)propionyl, 3-(2,4-dichlorophenyl)propionyl, 3-(2,4-difluorophenyl) propionyl, 3-(2,4-dibromophenyl)propionyl and 3-(2,4-diiodophenyl)propionyl groups, of which the p-chlorophenylacetyl group is most preferred.

Where $R^3$ represents an alkoxycarbonyl group, this may be a straight or branched chain alkoxycarbonyl group having from 1 to 6 carbon atoms in the alkoxy part, i.e. having a total of from 2 to 7 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and hexyloxycarbonyl groups, of which we prefer those alkoxycarbonyl group having from 2 to 4 carbon atoms and most prefer the ethoxycarbonyl group.

Where $R^4$ represents an alkyl group, this may be a straight or branched chain alkyl group having from 1 to 5 carbon atoms, such as the methyl, ethyl, propyl, isopropyl, butyl, isobutyl, t-butyl and pentyl groups, of which we prefer those alkyl groups having from 1 to 4 carbon atoms, more preferably a methyl or t-butyl group, and most preferably a methyl group.

Where $R^4$ or $R^5$ represents an alkoxy group, this may be a straight or branched chain alkoxy group having from 1 to 5 carbon atoms, such as the methoxy, ethoxy, propoxy, isopropoxy, butoxy, isobutoxy, t-butoxy and pentyloxy groups, of which we prefer those alkoxy groups having from 1 to 4 carbon atoms, more preferably a methoxy or t-butoxy group, and most preferably a methoxy group.

Where $R^4$ and $R^5$ together represent an alkylenedioxy group, this has from 1 to 4 carbon atoms and examples include the methylenedioxy, ethylenedioxy, propylenedioxy, trimethylenedioxy and tetramethylenedioxy groups, of which the methylenedioxy and ethylenedioxy groups are preferred.

n is 1, 2 or 3, but is preferably 1.

Y and Z are the same as or different from each other and each represents an oxygen atom or an imino group; however, both are preferably oxygen atoms.

Preferred compounds of the present invention are those compounds of formula (Ia):

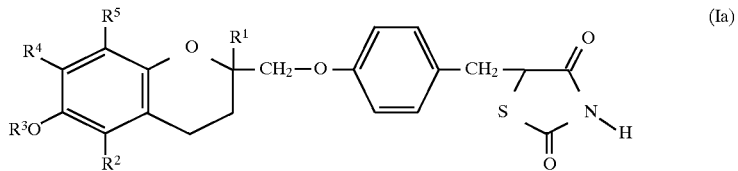

wherein:
$R^1$, $R^2$, $R^4$ and $R^5$ are the same as or different from each other and each represents a hydrogen atom or an alkyl group having from 1 to 5 carbon atoms; and
$R^3$ represents a hydrogen atom, an aliphatic acyl group having from 1 to 6 carbon atoms, a benzoyl group, a naphthoyl group, a benzoyl or naphthoyl group which is substituted by at least one substituent selected from the group consisting of substituents α, defined below, or an alkoxycarbonyl group having from 1 to 6 carbon atoms in the alkoxy part;
substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;
and pharmaceutically acceptable salts thereof Preferred classes of compounds of the present invention are those compounds of formula (I) or (Ia) and pharmaceutically acceptable salts thereof, in which:
(A) $R^1$ represents an alkyl group having from 1 to 4 carbon atoms.
(B) $R^2$ represents a hydrogen atom or an alkyl group having from 1 to 3 carbon atoms.
(C) $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.
(D) $R^4$ represents an alkyl group having from 1 to 4 carbon atoms.
(E) $R^5$ represents a hydrogen atom or an alkyl group having from 1 to 3 carbon atoms.

In particular, of the above compounds, we prefer those compounds of formula (I) and (Ia), in which $R^1$ is as defined in (A) above, $R^2$ is as defined in (B) above, $R^3$ is as defined in (C) above, $R^4$ is as defined in (D) above, and $R^5$ is as defined in (E) above.

More preferred classes of compounds of the present invention are those compounds of formula (I) and (Ia) and pharmaceutically acceptable salts thereof, in which:
(F) $R^1$ represents an alkyl group having from 1 to 4 carbon atoms.
(G) $R^2$ represents a hydrogen atom or an alkyl group having from 1 to 3 carbon atoms.
(H) $R^3$ represents a hydrogen atom, an acetyl group, a benzoyl group or an ethoxycarbonyl group.
(I) $R^4$ represents an alkyl group having from 1 to 4 carbon atoms.

(J) $R^5$ represents a hydrogen atom or an alkyl group having from 1 to 3 carbon atoms.

In particular, of the above compounds, we prefer those compounds of formula (I) and (Ia), in which $R^1$ is as defined in (F) above, $R^2$ is as defined in (G) above, $R^3$ is as defined in (H) above, $R^4$ is as defined in (I) above, and $R^5$ is as defined in (J) above.

The most preferred classes of compounds of the present invention are those compounds of formula (I) and (Ia) and pharmaceutically acceptable salts thereof, in which:

(K) $R^1$ represents a methyl group.

(L) $R^2$ represents a hydrogen atom or a methyl group.

(M) $R^3$ represents a hydrogen atom, an acetyl group or an ethoxycarbonyl group.

(N) $R^4$ represents a methyl or a t-butyl group.

(O) $R^5$ represents a hydrogen atom or a methyl group.

In particular, of the above compounds, we prefer those compounds of formula (I) and (Ia), in which $R^1$ is as defined in (K) above, $R^2$ is as defined in (L) above, $R^3$ is as defined in (M) above, $R^4$ is as defined in (N) above, and $R^5$ is as defined in (O) above.

When the compounds of the present invention contain at least one basic group in their molecules, they can thus form acid addition salts. Examples of such acid addition salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkanesulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. Such acid addition salts may readily be prepared by conventional means.

The compounds of the present invention can also form salts with cations, e.g. metals. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with methylamine, dimethylamine, triethylamine, diisopropylamine, cyclohexylamine or dicyclohexylamine; and salts with a basic amino acid, such as lysine or arginine. Such salts may likewise readily be prepared by conventional means.

The compounds of the present invention can exist in the form of various isomers.

Thus, the carbon atom at position 2 of the chromane ring and that at position 5 of the thiazolidine ring are both asymmetric carbon atoms. In each of the compounds of formula (I) and (Ia), stereoisomers due to these asymmetric carbon atoms as well as equimolar and non-equimolar mixtures thereof are all represented by only the one formula. Accordingly, the scope of the present invention covers all of these isomers separately, as well as all mixtures thereof.

In the compounds of formula (I) in which Y and Z both represent imino groups, in which Y and Z both represent oxygen atoms and in which one of Y and Z represents an oxygen atom and the other represents an imino group can exist in the form of various tautomers as explained in Japanese Patent Kokai Application Sho 60-51189, U.S. Pat. No. 4,572,912 and European Patent No. 139 421.

In each of the compounds of formula (I) and (Ia), the tautomers and equimolar and non-equimolar mixtures thereof are all represented by only the one formula. Accordingly, the scope of the present invention covers all of these tautomers and all mixtures thereof.

The compounds of the present invention can also form solvates (for example hydrates), and the present invention embraces all such solvates.

The present invention covers additionally all of the so-called "pro-drugs" which can be converted by metabolic change in vivo into any one of the compounds of formula (I) or salts thereof.

Specific examples of the compounds of formula (I) are those compounds of formula (Ia):

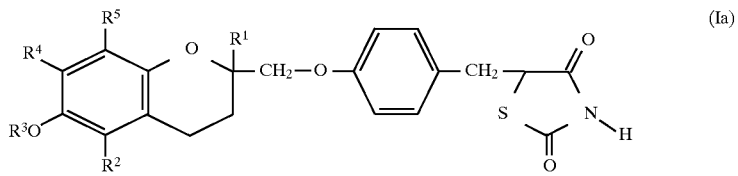

in which $R^1$, $R^2$, $R^3$, $R^4$ and $R^5$ are as defined in the following Table 1. In the Table, the following abbreviations are used:

Ac: acetyl,
iBu: isobutyl,
tBu: t-butyl,
Byr: butyryl,
Bz: benzoyl,
Etc: ethoxycarbonyl,
Et: ethyl,
Me: methyl,
Pn: pentyl.

TABLE 1

| Compound No. | $R^1$ | $R^2$ | $R^3$ | $R^4$ | $R^5$ |
|---|---|---|---|---|---|
| 1 | Me | Me | H | Me | Me |
| 2 | H | Me | H | Me | Me |
| 3 | Me | H | H | H | H |
| 4 | Me | H | H | tBu | H |
| 5 | Et | Me | H | Me | Me |
| 6 | iBu | Me | H | Me | Me |
| 7 | Pn | Me | H | Me | Me |
| 8 | Me | Me | Ac | Me | Me |
| 9 | Me | Me | Bz | Me | Me |
| 10 | Me | Me | Etc | Me | Me |
| 11 | Me | H | Ac | Me | H |
| 12 | Me | H | H | Me | H |
| 13 | Me | Me | Byr | Me | Me |

Of the compounds listed above, preferred compounds are Compounds No.:

1. 5-[4-(6-Hydroxy-2,5,7,8-tetramethylchroman-2-ylmethoxy)benzyl]thiazolidin-2,4-dione;
4. 5-[4-(6-Hydroxy-2-methyl-7-t-butylchroman-2-ylmethoxy)benzyl]thiazolidin-2,4-dione;
5. 5-[4-(6-Hydroxy-2-ethyl-5,7,8-trimethylchroman-2-ylmethoxy)benzyl]-thiazolidin-2,4-dione;

6. 5-[4-(6-Hydroxy-2-isobutyl-5,7,8-trimethylchroman-2-ylmethoxy)benzyl]-thiazolidin-2,4-dione;
8. 5-[4-(6-Acetoxy-2,5,7,8-tetramethylchroman-2-ylmethoxy)benzyl]thiazolidin-2,4-dione;
10. 5-[4-(6-Ethoxycarbonyl-2,5,7,8-tetramethylchroman-2-ylmethoxy)benzyl]-thiazolidin-2,4-dione;
and pharmaceutically acceptable salts thereof.

More preferred compounds are Compounds No. 1, 4 and 10, and the most preferred compound is Compound No. 1.

The compounds of the present invention are known compounds, and are described in, for example, Japanese Patent Kokai Application Sho 60-51189, U.S. Pat. No. 4,572,912 and European Patent No.0139421. They may be prepared as described in these documents or by other known methods.

The thiazolidine derivatives or pharmaceutically acceptable salts thereof of the present invention can be administered by various routes. The route of administration is not particularly limited, and is determined according to the drug preparation form, and the condition of the patient, such as the age, sex and the degree of disease. For example, when tablets, pills, powders, granules, syrups, liquid preparations, suspensions, emulsions or capsules are used, these may be administered orally. When injections are used, these may be injected intravenously by themselves or in admixture with the usual fluid replacements, such as glucose and amino acids; or they may be, if necessary, be administered intramuscularly, intracutaneously, subcutaneously or intraperitoneally by themselves. When suppositories are used, these may be administered intrarectally.

The compounds of the present invention may be administered alone or in admixture with any known additives commonly used in the field of drug preparation such as vehicles, binders, disintegrators, lubricants, solubilizers, corrigents and coating agents. Such preparations may be obtained by known means.

When tablets are to be prepared, carriers which are widely known in this field can be employed, for example: vehicles such as lactose, sucrose, sodium chloride, glucose, urea, starch, calcium carbonate, kaolin, crystalline cellulose and silicic acid; binders such as water, ethanol, propanol, simple syrup, glucose solution, starch solution, gelatine solution, carboxymethyl cellulose, purified shellac, methyl cellulose, potassium phosphate and polyvinylpyrrolidone; disintegrators such as dry starch, sodium alginate, agar powder, laminaran powder, sodium bicarbonate, calcium carbonate, polyoxyethylene sorbitan fatty acid esters, sodium laurylsulfate, stearic acid monoglyceride, starch and lactose; disintegration inhibitors such as sucrose, stearine, cacao oil and hydrogenated oil; absorption accelerators such as quaternary ammonium bases and sodium laurylsulfate; humectants such as glycerin and starch; adsorbers such as starch, lactose, kaolin, bentonite and colloidal silicic acid; and lubricants such as purified talc, a salt of stearic acid, powdery boric acid and polyethylene glycol. In addition, the tablets can be, if necessary, prepared as ordinary coated tablets such as sugar-coated tablets, gelatine-coated tablets, enteric coated tablets, film-coated tablets, or as double-layer tablets or multi-layer tablets.

When pills are to be prepared, carriers which are widely known in this field can be employed, for example: vehicles such as glucose, lactose, starch, cacao oil, hardened vegetable oil, kaolin and talc; binders such as gum arabic, tragacanth powder, gelatine and ethanol; and disintegrators such as laminaran agar.

When suppositories are to be prepared, carriers which are widely known in this field can be employed, for example: polyethylene glycol, cacao oil, a higher alcohol, a higher alcohol ester, gelatine and semi-synthetic glyceride.

When injections are to be prepared, they may be solutions, emulsions or suspensions which are preferably sterilised and isotonic to blood. When these solutions, emulsions and suspensions are to be prepared, diluents conventionally used in this field can be employed; for example, water, ethyl alcohol, propylene glycol, ethoxyisostearyl alcohol, polyoxy-isostearyl alcohol and a fatty acid ester of polyoxyethylene sorbitan. In this case, sufficient sodium chloride, glucose or glycerin to make the solution isotonic may be included in these preparations; or ordinary solubilizers, buffers or pain suppressers may be added.

In addition, coloring agents, preservatives, perfumes, flavors, sweetenings and any other drugs may be added, if necessary.

The amount of the active ingredient contained in these preparations is not particularly limited and may be selected over a wide range. In general, from 1 to 70% by weight, preferably from 1 to 30% by weight, of the active ingredient may be present in the whole composition.

Although the dosage may vary depending on the symptoms, age and body weight of the patient, as well as the route of administration and the form of the drug, an upper limit of 5,000 mg (preferably 1,000 mg, and more preferably 500 mg), and a lower limit of 5 mg (preferably 10 mg, and more preferably 50 mg), may be given daily to an adult human patient.

Osteoporosis may be assessed by a measurement of bone mineral density. Bone mineral density can be measured according to the method reported, for example, in Radioisotope, 37, (9), 521–524 (1988) or in Rinsho-Hoshasen, 35, (1), 41–48 (1990).

Alternatively, bone mineral density can be measured using the simple photon absorption method [Science, 142, 230–236 (1963)] or the quantitative CT method [Invest. Radiol. 12, 541–551 (1977)].

The efficacy of the compounds of the present invention was tested as described in the following Examples.

EXAMPLE 1

Measurement of Bone Mineral Density

Three groups of animals were tested:

1. Zucker Diabetic Fatty rats ("ZDF rats"): these are experimental animals with spontaneous diabetes mellitus. A test drug was administered to these animals in a conventional F2 powdery feed. This group is referred to as the "test ZDF group".
2. ZDF rats to which the F2 powdery feed is administered without the drug. This group is referred to as the "control ZDF group".
3. Normal experimental rats (i.e. not ZDF rats) to which the F2 powdery feed is administered without the drug. This group is referred to as the "normal group".

Compound No. 1, or 5-[4-(6-hydroxy-2,5,7,8-tetramethylchroman-2-ylmethoxy)benzyl]thiazolidin-2,4-dione, also known as "troglitazone", was administered to 6 week old ZDF rats, by mixing it into F2 powdery feed in an amount of 0.2% w/w for a period of 13 weeks. The mean dosage was 165 mg/kg/day. At this dose, diabetes is fully controlled. At 19 weeks of age, the rats were sacrificed by ether anesthesia followed by blood-letting from the abdominal aorta. The femoral bones were excised to measure their bone mineral density. For the measurement by X ray, Bone Mineral Density Measuring Apparatus (DCS-600R, Aloka, Japan) was employed.

The results are shown in Table 2.

TABLE 2

| | Bone mineral density (mg/cm$^2$) | |
|---|---|---|
| | Number of rats in group | BMD |
| Normal group | 7 | 187.3 ± 2.3*** |
| Control ZDF group | 7 | 164.6 ± 3.9 |
| Test ZDF group | 7 | 172.8 ± 7.2* |

1) The values of the bone mineral density are given by the mean value ± standard error.
2) * and *** indicate significant differences from the value of control ZDF rats at p < 0.05 and p < 0.001 respectively.

As is clearly shown in Table 2, the thiazolidine derivatives of the present invention and pharmaceutically acceptable salts thereof showed an excellent improvement on the bone mineral density.

EXAMPLE 2

Comparison of Effects of Troglitazone and Pioglitazone on Bone Mineral Density

The experiment reported in Example 1 was repeated, using 4 groups of rats:
1. A normal group (as in Example 1).
2. A control ZDF group (as in Example 1).
3. A test ZDF group in which troglitazone was present in the feed in an amount of 0.2%, resulting in an average uptake of 132 mg/kg/day (hereinafter the "troglitazone ZDF group").
4. A test ZDF group in which pioglitazone was present in the feed in an amount of 0.067%, resulting in an average uptake of 52.6 mg/kg/day (hereinafter the "pioglitazone ZDF group").

Pioglitazone is more active than troglitazone and so less is needed to achieve an anti-diabetic effect. At the doses used, both pioglitazone and troglitazone fully controlled diabetes in the ZDF rats.

The results are shown in Table 3.

TABLE 3

| | Bone mineral density (mg/cm$^2$) | |
|---|---|---|
| | Number of rats in group | BMD |
| Normal group | 6 | 187.4 ± 1.5 |
| Control ZDF group | 6 | 157.0 ± 2.2 |
| Troglitazone ZDF group | 6 | 169.4 ± 1.1*** |
| Pioglitazone ZDF group | 6 | 149.3 ± 1.8* |

1) The values of the bone mineral density are given by the mean value ± standard error.
2) * and *** indicate significant differences from the value of control ZDF rats at p < 0.05 and p < 0.001 respectively.

From these results it can be seen that the compound of the present invention (troglitazone) increased BMD from the depressed level in the control ZDF rats almost to the level found in normal rats. In contrast, pioglitazone reduced BMD to below the level found in untreated ZDF rats, thus indicating that it would have the unfortunate side effect of initiating or enhancing osteoporosis in diabetic mammals.

EXAMPLE 3

Comparison of Effects of Troglitazone and Pioglitazone on Bone Density

The experiment reported in Example 1 was repeated, but only for 4 weeks, using 6 groups of rats:

1. A normal group (as in Example 1).
2. A control ZDF group (as in Example 1).
3. A test ZDF group in which troglitazone was present in the feed in an amount of 0.05%, resulting in an average uptake of 43.5 mg/kg/day (hereinafter the "low troglitazone ZDF group").
4. A test ZDF group in which troglitazone was present in the feed in an amount of 0.1%, resulting in an average uptake of 89.8 mg/kg/day (hereinafter the "high troglitazone ZDF group").
5. A test ZDF group in which pioglitazone was present in the feed in an amount of 0.0125%, resulting in an average uptake of 12.4 mg/kg/day (hereinafter the "low pioglitazone ZDF group").
6. A test ZDF group in which pioglitazone was present in the feed in an amount of 0.025%, resulting in an average uptake of 23.1 mg/kg/day (hereinafter the "high pioglitazone ZDF group").

At these doses, troglitazone and pioglitazone do not control diabetes or control it only partially.

The results are shown in Table 4.

TABLE 4

| | Bone mineral density (mg/cm$^2$) | |
|---|---|---|
| | Number of rats in group | BMD |
| Normal group | 10 | 153.4 ± 0.9 |
| Control ZDF group | 5 | 149.8 ± 1.0 |
| Low troglitazone ZDF group | 5 | 156.6 ± 1.5*** |
| High troglitazone ZDF group | 5 | 159.8 ± 1.2*** |
| Low pioglitazone ZDF group | 5 | 151.2 ± 0.9 |
| High pioglitazone ZDF group | 5 | 151.2 ± 0.7 |

1) The values of the bone mineral density are given by the mean value ± standard error.
2) *** indicates a significant difference from the value of control ZDF rats at p < 0.001.

From these results it can be seen that only troglitazone improves BMD as compared with the control ZDF group, while pioglitazone is not effective. However, at these doses, both troglitazone and pioglitazone are incompletely effective against diabetes.

EXAMPLE 4

Acute Toxicity

The acute toxicity of troglitazone was examined by a conventional procedure.

To 3 ddy-mice, a dose of 300 mg/kg of troglitazone was administered orally. After 5 days, all mice were alive.

The acute toxicities of Compounds Nos. 2, 3, 4 and 10 were examined in a similar way by oral administration. The acute toxicity values were all found to be more than 300 mg/kg.

PREPARATION

Capsule Preparation

The following ingredients were filled in a gelatine capsule:

| | |
|---|---|
| Compound No. 1 | 100 mg |
| Lactose | 168.3 mg |

| | |
|---|---|
| Corn starch | 70 mg |
| Magnesium stearate | 1.7 mg |
| Total | 340 mg |

We claim:

1. A method of treating or preventing osteoporosis in a subject in need thereof, comprising administering to said subject an amount of a thiazolidine compound sufficient to treat or prevent osteoporosis, said thiazolidine compound being selected from the group consisting of compounds of formula (I):

$$\text{(I)}$$

wherein:

$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms;

n is 1, 2 or 3;

Y and Z are the same as or different from each other and each represents an oxygen atom or an imino group; and substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

2. The method of claim 1, wherein $R^1$ represents an alkyl group having from 1 to 4 carbon atoms.

3. The method of claim 1, wherein $R^2$ represents a hydrogen atom or an alkyl group having from 1 to 3 carbon atoms.

4. The method of claim 1, wherein $R^3$ represents a hydrogen atom, an aliphatic acyl group having from 1 to 4 carbon atoms, an unsubstituted benzoyl or naphthoyl group or an alkoxycarbonyl group having from 2 to 4 carbon atoms.

5. The method of claim 1, wherein $R^4$ represents an alkyl group having from 1 to 4 carbon atoms.

6. The method of claim 1, wherein $R^5$ represents a hydrogen atom or an alkyl group having from 1 to 3 carbon atoms.

7. The method of claim 1, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms;

$R^4$ represents an alkyl group having from 1 to 4 carbon atoms; and $R^5$ represents a hydrogen atom or an alkyl group having from 1 to 3 carbon atoms.

8. The method of claim 1, wherein $R^3$ represents a hydrogen atom, an acetyl group, a benzoyl group or an ethoxycarbonyl group.

9. The method of claim 1, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an acetyl group, a benzoyl group or an ethoxycarbonyl group;

$R^4$ represents an alkyl group having from 1 to 4 carbon atoms; and $R^5$ represents a hydrogen atom or an alkyl group having from 1 to 3 carbon atoms.

10. The method of claim 1, wherein $R^1$ represents a methyl group.

11. The method of claim 1, wherein $R^2$ represents a hydrogen atom or a methyl group.

12. The method of claim 1, wherein $R^3$ represents a hydrogen atom, an acetyl group or an ethoxycarbonyl group.

13. The method of claim 1, wherein $R^4$ represents a methyl or a t-butyl group.

14. The method of claim 1, wherein $R^5$ represents a hydrogen atom or a methyl group.

15. The method of claim 1, wherein:

$R^1$ represents a methyl group;

$R^2$ represents a hydrogen atom or a methyl group;

$R^3$ represents a hydrogen atom, an acetyl group or an ethoxycarbonyl group;

$R^4$ represents a methyl or a t-butyl group; and $R^5$ represents a hydrogen atom or a methyl group.

16. The method of claim 1, wherein Y represents an oxygen atom.

17. The method of claim 1, wherein Z represents an oxygen atom.

18. The method of claim 1, wherein Y and Z both represent oxygen atoms.

19. The method of claim 1, wherein n is 1.

20. The method of claim 1, wherein said thiazolidine compound is selected from the group consisting of:

5-[4-(6-Hydroxy-2,5,7,8-tetramethylchroman-2-ylmethoxy)benzyl]thiazolidin-2,4-dione;

5-[4-(6-Hydroxy-2-methyl-7-t-butylchroman-2-ylmethoxy)benzyl]thiazolidin-2,4-dione;

5-[4-(6-Hydroxy-2-ethyl-5,7,8-trimethylchroman-2-ylmethoxy)benzyl]thiazolidin-2,4-dione;

5-[4-(6-Hydroxy-2-isobutyl-5,7,8-trimethylchroman-2-ylmethoxy)benzyl]thiazolidin-2,4-dione;

5-[4-(6-Acetoxy-2,5,7,8-tetramethylchroman-2-ylmethoxy)benzyl]thiazolidin-2,4-dione;

5-[4-(6-Ethoxycarbonyl-2,5,7,8-tetramethylchroman-2-ylmethoxy)benzyl]thiazolidin-2,4-dione;

and pharmaceutically acceptable salts thereof.

21. The method of claim 1, wherein said thiazolidine compound has the formula (Ia):

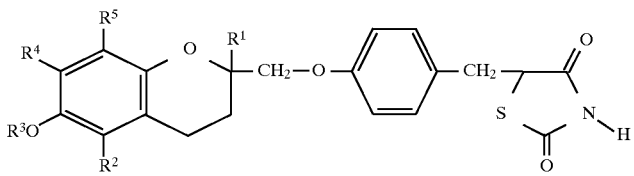

(Ia)

wherein $R^1$, $R^2$, $R^3$, $R^4$ and $R^5$ are as defined in claim 1.

22. The method of claim 21, wherein $R^1$ represents an alkyl group having from 1 to 4 carbon atoms.

23. The method of claim 21, wherein $R^2$ represents a hydrogen atom or an alkyl group having from 1 to 3 carbon atoms.

24. The method of claim 21, wherein $R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms.

25. The method of claim 21, wherein $R^4$ represents an alkyl group having from 1 to 4 carbon atoms.

26. The method of claim 21, wherein $R^5$ represents a hydrogen atom or an alkyl group having from 1 to 3 carbon atoms.

27. The method of claim 21, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an aliphatic acyl group having from 1 to 4 carbon atoms, an unsubstituted benzoyl or naphthoyl group, or an alkoxycarbonyl group having from 2 to 4 carbon atoms;

$R^4$ represents an alkyl group having from 1 to 4 carbon atoms; and $R^5$ represents a hydrogen atom or an alkyl group having from 1 to 3 carbon atoms.

28. The method of claim 21, wherein $R^3$ represents a hydrogen atom, an acetyl group, a benzoyl group or an ethoxycarbonyl group.

29. The method of claim 21, wherein:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an acetyl group, a benzoyl group or an ethoxycarbonyl group;

$R^4$ represents an alkyl group having from 1 to 4 carbon atoms; and $R^5$ represents a hydrogen atom or an alkyl group having from 1 to 3 carbon atoms.

30. The method of claim 21, wherein $R^1$ represents a methyl group.

31. The method of claim 21, wherein $R^2$ represents a hydrogen atom or a methyl group.

32. The method of claim 21, wherein $R^3$ represents a hydrogen atom, an acetyl group or an ethoxycarbonyl group.

33. The method of claim 21, wherein $R^4$ represents a methyl or a t-butyl group.

34. The method of claim 21, wherein $R^5$ represents a hydrogen atom or a methyl group.

35. The method of claim 21, wherein:

$R^1$ represents a methyl group;

$R^2$ represents a hydrogen atom or a methyl group;

$R^3$ represents a hydrogen atom, an acetyl group or an ethoxycarbonyl group;

$R^4$ represents a methyl or a t-butyl group; and $R^5$ represents a hydrogen atom or a methyl group.

36. The method of claim 1, wherein said thiazolidine compound is 5-[4-(6-hydroxy-2,5,7,8-tetramethylchroman-2-ylmethoxy)benzyl]-thiazolidin-2,4-dione.

37. A method of treating osteoporosis in a patient also suffering from diabetes, comprising administering to said patient an amount of a thiazolidine compound sufficient to treat both osteoporosis and diabetes, said thiazolidine compound being selected from the group consisting of compounds of formula (I):

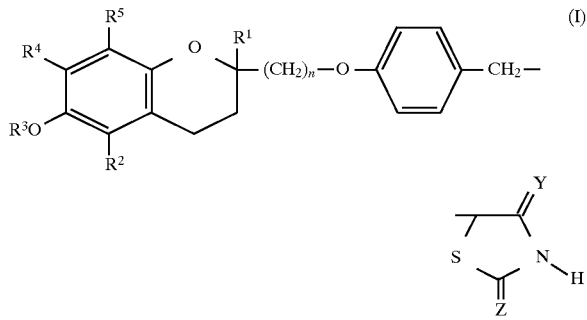

(I)

wherein:

$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms;

n is 1, 2 or 3;

Y and Z are the same as or different from each other and each represents an oxygen atom or an imino group; and substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

38. The method of claim 37, wherein said diabetes is non-insulin dependent diabetes.

39. The method of claim 37, wherein said thiazolidine compound is 5-[4-(6-hydroxy-2,5,7,8-tetramethylchroman-2-ylmethoxy)benzyl]-thiazolidin-2,4-dione.

40. A method of treating osteoporosis in a patient also suffering from diabetes, comprising administering to said patient an amount of thiazolidine compound sufficient to treat both osteoporosis and diabetes, said thiazolidine compound being selected from the group consisting of compounds of formula (Ia):

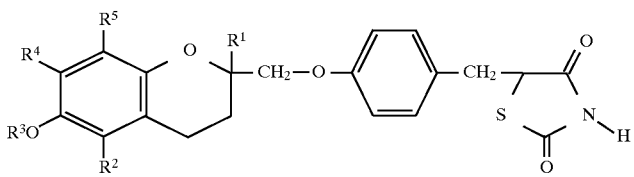

(Ia)

wherein:

$R^1$ and $R^2$ are the same as or different from each other and each represents a hydrogen atom or an alkyl group having from 1 to 5 carbon atoms;

$R^3$ represents a hydrogen atom, an aliphatic acyl group having from 1 to 6 carbon atoms, a cycloalkanecarbonyl group having from 5 to 7 carbon atoms in the cycloalkane part, a benzoyl group, a naphthoyl group, a benzoyl or naphthoyl group which is substituted by at least one substituent selected from the group consisting of substituents α, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group which is substituted by at least one halogen substituent, a cinnamoyl group, an alkoxycarbonyl group having from 1 to 6 carbon atoms in the alkoxy part or a benzyloxycarbonyl group;

$R^4$ and $R^5$ are the same as or different from each other and each represents a hydrogen atom, an alkyl group having from 1 to 5 carbon atoms or an alkoxy group having from 1 to 5 carbon atoms, or $R^4$ and $R^5$ together represent an alkylenedioxy group having from 1 to 4 carbon atoms; substituents α are selected from the group consisting of alkyl groups having from 1 to 4 carbon atoms, alkoxy groups having from 1 to 4 carbon atoms, halogen atoms, hydroxy groups, amino groups, alkylamino groups having from 1 to 4 carbon atoms, dialkylamino groups having from 1 to 4 carbon atoms in each alkyl part, and nitro groups;

and pharmaceutically acceptable salts thereof.

41. The method of claim 40, wherein said diabetes is non-insulin dependent diabetes.

\* \* \* \* \*